United States Patent

Keens et al.

Patent Number: 5,923,422
Date of Patent: Jul. 13, 1999

[54] METHOD OF OBTAINING AN OPTICAL FT SPECTRUM

[75] Inventors: Axel Keens, Karlsruhe; Norbert Rapp, Hagenbach, both of Germany

[73] Assignee: Bruker Analtyik GmbH, Rheinstetten, Germany

[21] Appl. No.: 09/017,172

[22] Filed: Feb. 2, 1998

[30] Foreign Application Priority Data

Feb. 7, 1997 [DE] Germany ............................. 19704598

[51] Int. Cl.⁶ .................................................. G01B 9/02
[52] U.S. Cl. .......................................... 356/346; 356/349
[58] Field of Search ..................................... 356/346, 349

[56] References Cited

U.S. PATENT DOCUMENTS 5,491,548  2/1996  Bell et al. ............................... 356/73.1

OTHER PUBLICATIONS

Applied Optics, vol. 35, No. 16 (Jun. 1, 1996): James W. Brault "New approach to high–precision Fourier transform spectrometer design".

Werner Herres and J. Gronholz: "Datenverarbeitung in der FT–IR–Spektroskopie" in Comp. Anw. Lab., No. 5/1984, pp. 352–356, vol. 6/1984, pp. 418–425 and vol. 5/1985, pp. 230–240.

Andreas Antoniou: "Digital Filters: Analysis and Design", McGraw–Hill Inc., 1979, pp. 171–175.

*Primary Examiner*—Robert H. Kim
*Assistant Examiner*—Andrew H. Lee
*Attorney, Agent, or Firm*—Paul Vincent

[57] ABSTRACT

A method of obtaining an FT spectrum according to Brault is improved in that the compensation filter is determined by recording a broad-band effective interferogram, carrying out complex Fourier transformation, forming a mean value of the phase spectra, converting the abscissa values into electrical frequencies, and establishing the transfer function of the detector and of the further signal processing elements, wherein the free parameters of the transfer function are chosen such that the phase response of the transfer function deviates as little as possible from the mean value of the phase spectrum of the effective recorded interferogram. If necessary, the determined transfer function is then digitized. The compensation filter is then determined as the inverse of the discrete transfer function. In this way, deconvolution of the signal processing elements transfer function from the spectra is facilitated in a particularly simple and effective manner.

10 Claims, 3 Drawing Sheets

METHOD OF OBTAINING AN OPTICAL FT SPECTRUM

This application claims Paris Convention priority of German patent application number 197 04 598.7 filed Feb. 7, 1997, the complete disclosure of which is hereby incorporated by reference.

BACKGROUND OF THE INVENTION

The invention concerns a method of obtaining a spectrum in an optical Fourier transform (FT) spectrometer with an interferometer and a detector for recording optical signals from the interferometer and converting into electrical signals, and also, if necessary, further signal processing elements, wherein an interferogram in an interesting wave length range (=effective interferogram) and a reference interferogram in a narrow-band reference wave length range are recorded simultaneously or with fixed phase shift, wherein the effective interferogram is digitized in a time-equidistant manner and wherein a digital compensation filter is applied to the sampled effective signals which compensates the complex frequency response consisting of the amplitude and phase responses of the detector and of all further signal processing elements.

A method of this type is known from the article titled "New approach to high-precision Fourier transform spectrometer design" by J. W. Brault in the journal Appl. Optics, Vol. 35, No. 16, pages 2891–2896, Jun. 1, 1996.

Optical spectroscopy, in particular infrared Fourier transform (IR-FT) spectroscopy is one of the most effective tools available to the analytical chemist in research, application and process control. Common methods of recording such optical spectra are described in all details e.g. in a series of articles by J. Gronholz and W. Herres with the title "Datenverarbeitung in der FT-IR-Spectroskopie" (data processing in FT-IR spectroscopy) in the journal Comp.Anw.Lab., Edition 5/1984, pages 352–356, Edition 6/1984, pages 418–425 and Edition 5/1985, pages 230–240. In this connection, zero crossings of a reference interferogram, which is recorded e.g. by an HeNe laser, are measured in their temporal sequence and the simultaneously recorded effective interferogram is digitized at these zero positions.

The hitherto common method, applied in optical FT spectrometers from the infrared to the ultraviolet range, of sampling the detector signal at equal intervals of optical path difference with reference to the position of the interferometer mirror (in a Michelson interferometer), however, does not allow exact compensation of the amplitude and phase responses of the detector, since the actual speed of the interferometer mirror is not known. For this reason, it is not possible to compensate differences and distortions of the transit time between effective signal and reference signal due to an apparatus function. Any speed variation of the mirror drive will therefore cause side band modulation in the spectral lines. For this reason, operational methods for spectrometers of this type are not suited for systems with heavy mechanical disturbances, e.g. in the vicinity of vibration generating machines or for spectrometers which are mounted e.g. on movable vehicles.

The initially cited publication by J. W. Brault describes, in contrast thereto, a method of compensating the amplitude and phase responses which can be used with particular efficiency in a system with time-equidistant sampling of the optical signal. By means of "pre"digitization of the effective signal with fixed time periods by means of an analog-to-digital converter (ADC), the apparatus function of the detector and the further signal processing elements can essentially be removed from the spectra by deconvolution. In the following, the method according to J. W. Brault is described in detail:

The time-equidistant sampling enables determination of the development with time of the detector signal. A digital filter (called compensation filter) can be applied to said sampled signal, which filter comprises the reciprocal complex frequency response (consisting of amplitude and phase responses) of the detector and the further signal processing elements. At the output of this filter, values are obtained which correspond to the optical signal at the input of the detector multiplied by its spectral responsivity delayed merely by a constant time period. The signal is independent of the driving speed of the interferometer mirror.

In order to obtain from the detector signal an interferogram which is independent of the speed variations of the movable mirror in the interferometer, spatially equidistant sampling of the IR detector signal is necessary. In order to convert the signal, which was sampled at equal time intervals, into a spatially equidistantly sampled signal, signal values are calculated by means of a digital filter with constant delay (called an interpolation filter) at those points in time, at which the optical path difference in the interferometer achieves certain values, i.e. values, at which the movable mirror/s in the interferometer is/are at certain locations.

Since the compensation filter and the interpolation filter operate in the time domain in each case, they can be applied one after the other.

Since the two filters are applied one after the other and both are time domain filters, they can be combined in one filter by convolving their filter coefficients. This reduces the requirements concerning the storage need and the speed of the digital filter processor.

Finally, a further digital filter (called spatial frequency filter) can be applied to the resulting values of the combined compensation and interpolation filter, which carries out reduction of the data to the desired spectral range. This filter cannot be linked with the combined filter since it has to be applied to spatially equidistant sampling values; however, it can be carried out by the same processor.

A particular advantage of the Brault method consists in the fact that extremely cheap ADCs from mass production in audio technology can be used. This time-equidistant sampling method enables simultaneous recording of the variations in time and the absolute positions of the zero crossings of the reference signal. After corresponding conversion of the ADC signals to spatially equidistant positions of the mirror (interpolation filter), a signal quality can be achieved which is at least equal to the one of the above-described spatially equidistant sampling method, wherein, however, the experimenter is given a considerably higher degree of flexibility since not only the zero crossings, but also any intermediate values can be employed for digitization. A further very important advantage of the Brault method is the possible correction of the apparatus function by means of the above-described compensation filter which corresponds to a deconvolution of the transfer function of the detector from the spectra.

In contrast thereto, it is the object of the present invention to provide a method on the basis of the suggestion by Brault, in which an essential component, namely the detection of the compensation filter and thus the deconvolution of the transfer function of the detector and the signal processing elements from the spectra is rendered possible in a particularly effective manner by means as simple as possible.

SUMMARY OF THE INVENTION

According to the invention, this object is achieved in connection with the initially described features of the method in that the compensation filter is determined for each of the utilized combinations of detector and further signal processing elements at least once by the following steps:

(a) Recording of at least one broad-band effective interferogram, in each case, during increase and decrease of the optical path difference in the interferometer carried out preferably at a constant speed, carrying out the complex Fourier transformation of the effective interferograms, forming the mean value of the phase spectra of the recorded effective interferograms and conversion of the abscissa values of the averaged phase spectrum into electrical frequencies;

(b) Establishing the usually rational transfer function of the detector and of the further signal processing elements, wherein the free parameters of the transfer function are chosen such that the phase response of the transfer function deviates as little as possible from the mean value of the phase spectrum of the effective interferograms recorded according to step (a);

(c) If necessary digitization of the transfer function determined according to step (b) by transformation into the Z-domain; and (d) Determination of the compensation filter as the inverse of the discrete transfer function.

The method according to the invention is to be used in FT spectrometers, in particular in the IR range. The spatially equidistant sampling of the detector signal which was common in former times and still is, does not allow exact compensation of the amplitude and phase responses of the detector such that any speed variation of the mirror drive in the interferometer generates side band modulation in the spectral lines. With the method according to the invention, particularly efficient compensation of the amplitude and phase responses is possible due to the time-equidistant sampling of the optical signal. In order to utilize said compensation filter, it has to be determined at least once for each detector, and possible further signal processing elements, to be used in the FT spectrometer.

An interferogram is recorded during the forward motion and the backward motion of the interferometer mirror in each case. Fourier transformation is carried out according to amplitude and phase. The phase spectra of the forward and backward motions are then added and divided by two (formation of the mean value). The optical phase generated by optical influences reverses with the direction of travel and cancels accordingly. The pure electrical phase response of the detector including the further signal processing elements is detected, while the optical characteristics are eliminated.

Then, a mathematical model of the transfer function of the signal processing elements including detector is established on the basis of their electrical properties, wherein the free parameters of the transfer function, i.e. the characteristic frequencies are determined by a fit method applied to the measured phase response. The transfer function determined in this manner, which is usually analog, is transferred to the discrete Z-domain and finally the compensation filter is detected as the inverse of the discrete transfer function. If the transfer function was established in step (b) already as discrete function in the Z-domain, step (c) will be omitted.

One variant of the inventive method is particularly preferred, in which, when increasing and decreasing the optical path difference, the optical path is selected symmetrically around zero path difference of the effective interferogram. In this manner, the phase spectra can be determined with a particularly high degree of accuracy.

In order to cover a possibly large electrical frequency range, several effective interferograms with different speeds for increasing and decreasing the optical path are recorded.

In an advantageous further development of these method variants, the abscissa values of the phase spectra of the recorded effective interferograms are converted into electrical frequencies in each case, and the individual measuring results are averaged to a common phase response.

Mathematical standard methods for adapting free parameters to predetermined curve shapes are used in one variant of the method which is distinguished in that for carrying out step (b) of the method, the transfer function is chosen in the linear factor representation in the Laplace domain and, on the basis of a uniform transfer function, poles and zeroes, the values of which are determined successively according to the method of the smallest error squares ("Least-Square-Fit" between phase response of the transfer function and mean value of the phase spectrum of the effective interferograms recorded according to step (a)), are added until further improvement of the Least-Square-Fit can no longer be achieved.

In a further advantageous variant of the method, the possibly necessary digitization of the transfer function is effected in step (c) of the method by means of a bilinear transformation, the sampling frequency of which corresponds to the sampling frequency of the effective interferogram. The result is a non-linear compression of the infinite analog frequency range to a finite discrete range from O to the sampling frequency.

A further advantageous variant of the method according to the invention consists in that in step (d) of the method, in which the compensation filter is derived from the discrete transfer function, a number of lowpass filters are applied to the compensation filter, where the number is equal to the difference in the orders of the numerator and the denominator of the analog transfer function. In this manner, it is possible to effectively suppress the interferences occurring due to digitizing at half sampling frequency.

A further development of this method variant is particularly advantageous, in which each lowpass filter is a FIR- ("finite impulse response") filter, preferentially of third order which results in a particularly high suppression of interferences.

In a preferred variant of the inventive method, stabilization of the compensation filter is achieved by elimination of instabilities of individual poles of the compensation filter by means of the Antoniou method by formation of inverse values of the poles. The mathematical effect of the Antoniou method is described in detail in the textbook by Andreas Antoniou with the title "Digital Filters: Analysis and Design", McGraw-Hill Inc., 1979, pages 171 to 175.

A further particularly preferred variant of the method finally consists in that implementation of the compensation filter and possible further filters, e.g. an interpolation filter and/or a spatial frequency filter is effected on a digital signal processor (DSP) and that the output data is transferred via digital interfaces to a computer for further processing. The signals at the output of the DSP are compatible with the signals of common devices with spatially equidistant sampling, such that already existing conventional evaluation software can be used without any problems. Furthermore, when calculating the filter/s, approximation is not required as it would be necessary e.g. with operation on a personal computer for reducing the calculation time.

Further advantages of the invention can be derived from the description and the drawing. The features mentioned above and below may be used in accordance with the invention individually or collectively in arbitrary combination. The embodiments shown and described are not be understood as exhaustive enumeration but rather have exemplary character for illustrating the invention.

The invention is shown in the drawing and is explained in further detail with respect to embodiments. In the drawing:

DESCRIPTION OF THE PREFERRED EMBODIMENT

Figure 1:
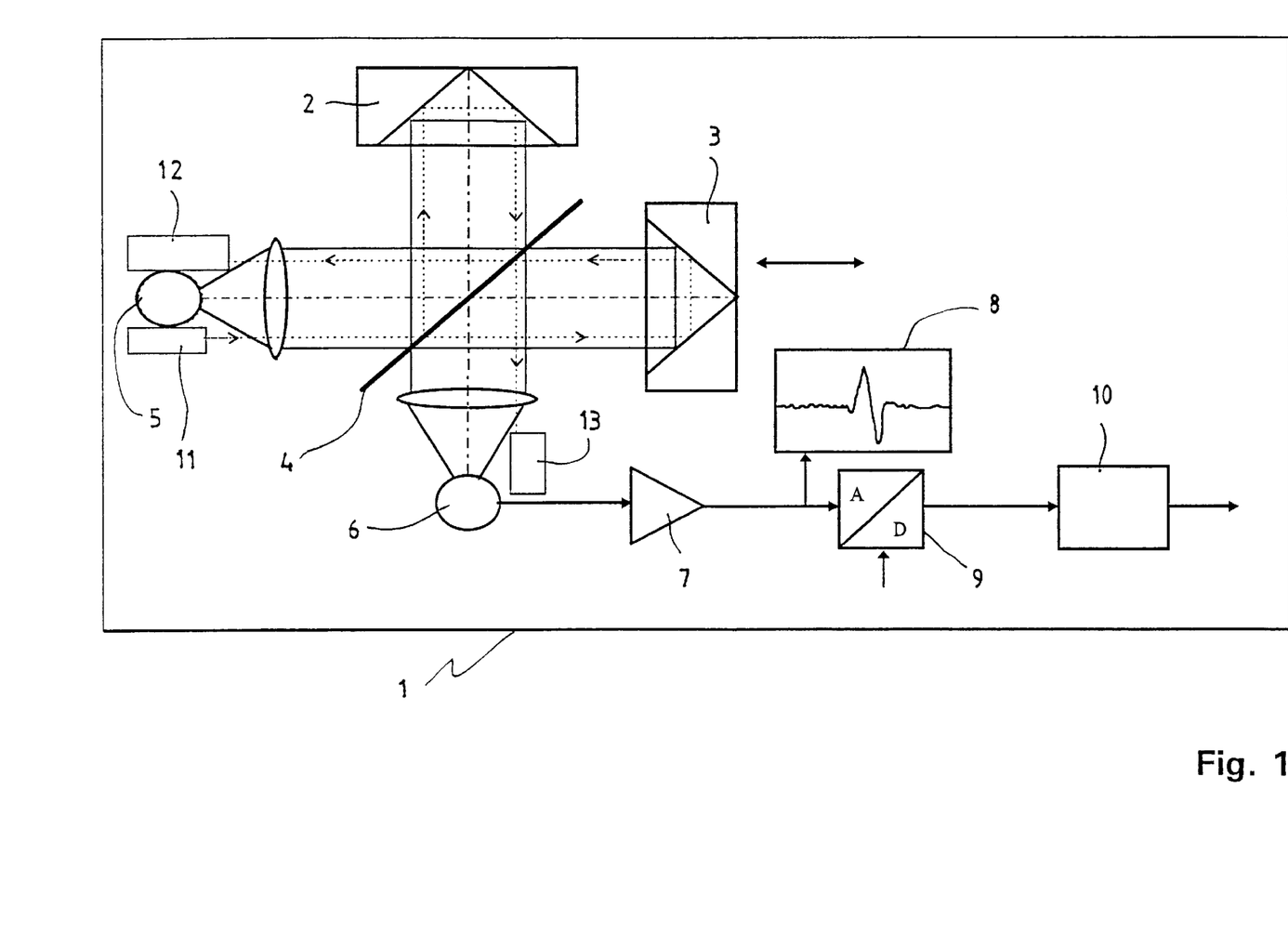
FIG. 1 shows a schematic representation of a Fourier transform spectrometer with Michelson interferometer for application of the method according to the invention.

The FT spectrometer 1 shown in FIG. 1 in a highly abstract functional diagram contains a Michelson interferometer with a fixed mirror 2 and a mirror 3 movable in the direction of the double arrow, which are supplied with light from an optical source 5 via a beam splitter 4, which is detected at a detector 6 after passage through the interferometer. The optical signals detected in the detector 6 are supplied to further signal processing elements 7 which may comprise e.g. an amplifier and at the output of which an analog effective interferogram 8 can be read. This is supplied to an analog-to-digital converter (ADC) 9 which is clocked at a fixed digitization frequency. The corresponding output signal from the ADC 9 is finally supplied to a compensation filter 10 which may be provided in particular in the form of suitable software on a computer not shown in the drawing, and is the focus of the present invention.

A laser 11, generally a HeNe laser supplies light to the interferometer for recording a reference interferogram. A first laser detector 12 receives the reference light reflected (back) from the interferometer, whereas a second laser detector 13 can detect the reference light emerging from the interferometer in the direction of the detector 6.

The possibility of time-equidistant interferogram sampling shown by J. W. Brault suffers from side band modulation distortions in the spectrum if the mirror speed is not constant as already mentioned before. In practice, one has always to count with external disturbances and thus variations in speed. The side band modulations can be avoided if the complex frequency response of the detector and the further signal processing elements is neutralized by a suitable compensation filter. In the following, the method for determining said compensation filter is explained.

(a) By means of the detector for which the compensation filter is to be determined, an interferogram with as large a band width as possible with an empty sample chamber is recorded. The optical mirror speed v should correspond to the value which is usual for this detector. A moderate spectral resolution, e.g. 4 cm$^{-1}$ in the MIR is sufficient since the phase to be detected is in general a slowly changing function. In order to keep the phase error as small as possible, the optical path should be arranged symmetrically around the maximum of the interferogram.

It is advisable to average over a large number of interferograms in order to achieve a good signal-to-noise ratio. One sum interferogram $I_j$ is determined during the forward motion of the mirror and another one during the backward motion. These sum interferograms are subjected separately to Fourier transformation:

$$S_j(m \cdot \Delta \nu) = \sum_{n=0}^{N-1} I_j(n \cdot \Delta x) \cdot \exp(i \cdot 2\pi nm / N);$$

wherein the forward and backward motions are indicated with "j" and the following designations are used:

m: travelling index of the frequency in the FT;
Δυ: optical frequency interval;
υ: optical frequency measured in wave numbers;
Δx: sampling interval;
$I_j$: interferogram intensity;
n: travelling index of the sampling points in the interferogram;
N: total number of the sampling points in the interferogram.

The phase generated by optical influences reverses with the direction of travel, the phase caused by the detector and further signal processing elements is independent of the direction of travel owing to causality. The optical phase is neutralized by forming the mean value of the phase spectra of the two directions of travel. This requires that the interferograms are sampled for both directions of travel at exactly the same values of the optical path difference and that the backward interferogram is not reversed. The corresponding phases are designated in the following by "φ".

φ$_j$(υ)=arctan[Im(S$_j$(υ))/Re(S$_j$(υ))]; υ=m·Δυ,

φ$_{fwd}$(υ)=φ$_{opt}$(υ)+φ$_{el}$(υ)

φ$_{bwd}$9υ)=-φ$_{opt}$(υ)+φ$_{el}$(υ)

$$\overline{\varphi}(\nu) = \frac{1}{2} \cdot (\varphi_{fwd}(\nu) + \varphi_{bwd}(\nu)) = \varphi_{el}(\nu)$$

Now, the abscissa is converted to electrical frequencies f:

Φ(f)=φ(υ); with f=v·υ

In order to <now the phase spectrum in a frequency range as broad as possible, all above-mentioned steps are repeated for as many different optical speeds $v_i$ as possible, which are selected such that a certain overlap is generated in the electrical frequencies of the associated phase spectra Φ$_i$(f). The different phase spectra Φ$_i$(f) are summarized to a mean value Φ(f).

(b) The detector and the further signal processing elements represent an analog transfer system which contains (ideally) only linear, concentrated and constant network elements. In this manner, it can be described necessarily and sufficiently by a rational transfer function H(s) with real coefficients. One of the representations equivalent thereto is the linear factor representation which is appropriately used to describe this analog system.

$$H(s) = k \cdot \frac{(s - N1) \cdot (s - N2) \cdot \ldots (s - Nl)}{(s - P1) \cdot (s - P2) \cdot \ldots (s - Pq)}$$

In this connection "s" designates the frequency variable in the Laplace domain; N1 . . . Nl are the zeroes; P1 . . . Pq are the poles.

This linear factor representation may be decomposed formally into the elementary systems "real pole", "real zero", "conjugate complex pole pair" and "conjugate complex zero pair".

Based on the phase deviation ΔΦ, i.e. the difference between the maximum value and the minimum value of the phase spectrum Φ(f), the minimum number r of the required elementary systems can be determined to $$r = \frac{\Delta\Phi}{\pi/2} \text{ (to be rounded up in whole numbers)}$$

Since the phase spectrum is known only in a limited frequency range, the number of the scheduled elementary systems has to be increased by two in order to be able, if necessary, to reproduce also the phase response occurring outside of this frequency range.

For all combinations of elementary systems (the conjugate complex pairs count as 2 elementary systems) which are possible with this given number, the following iteration steps are carried out now:

(1) Variation of the characteristic frequency of an elementary system in discrete steps between 0 and 10 $f_{max}$, wherein $f_{max}$ is the highest frequency of the phase spectrum Φ(f).
(2) Calculation of the mean error squares between the phase spectrum Φ(f) and the phase of the transfer function H(s); storing the characteristic frequency if the mean error squares are smaller than the minimum up to then.
(3) Continuation with (1) until the absolute minimum has been found.
(4) The absolute minimum is held as characteristic frequency of this elementary system and the elementary system is introduced into the transfer function as fixed component.
(5) Continue with the next elementary system using step (1).
(6) When all elementary systems have been determined, steps (1)–(5) can be repeated with a finer frequency pattern, if necessary.

The final transfer function is the one which has the smallest error squares of all possible combinations of elementary systems.

In practice, certain unreasonable combinations can be excluded from the start in order to limit the calculation effort.

The phase spectrum of the DTGS detector (=original phase) (mentioned as an example) can be best described by the phase of the following transfer function (=calculated phase):

$$H(s) = \frac{(k1 \cdot s) \cdot (k2 \cdot s)}{(k1 \cdot s + 1) \cdot (k2 \cdot s + 1) \cdot (k3 \cdot s + 1) \cdot (k4 \cdot s + 1)} \text{ with}$$

| Constant | k1 | k2 | k3 | k4 |
|---|---|---|---|---|
| Value in ω [rad/s] | 8.69 | 91.23 | 174.64 | 54327 |
| Value in f = ω/2π [Hz] | 1.38 | 14.51 | 27.79 | 8646.41 | wherein ω designates an angular frequency.

Figure 2:
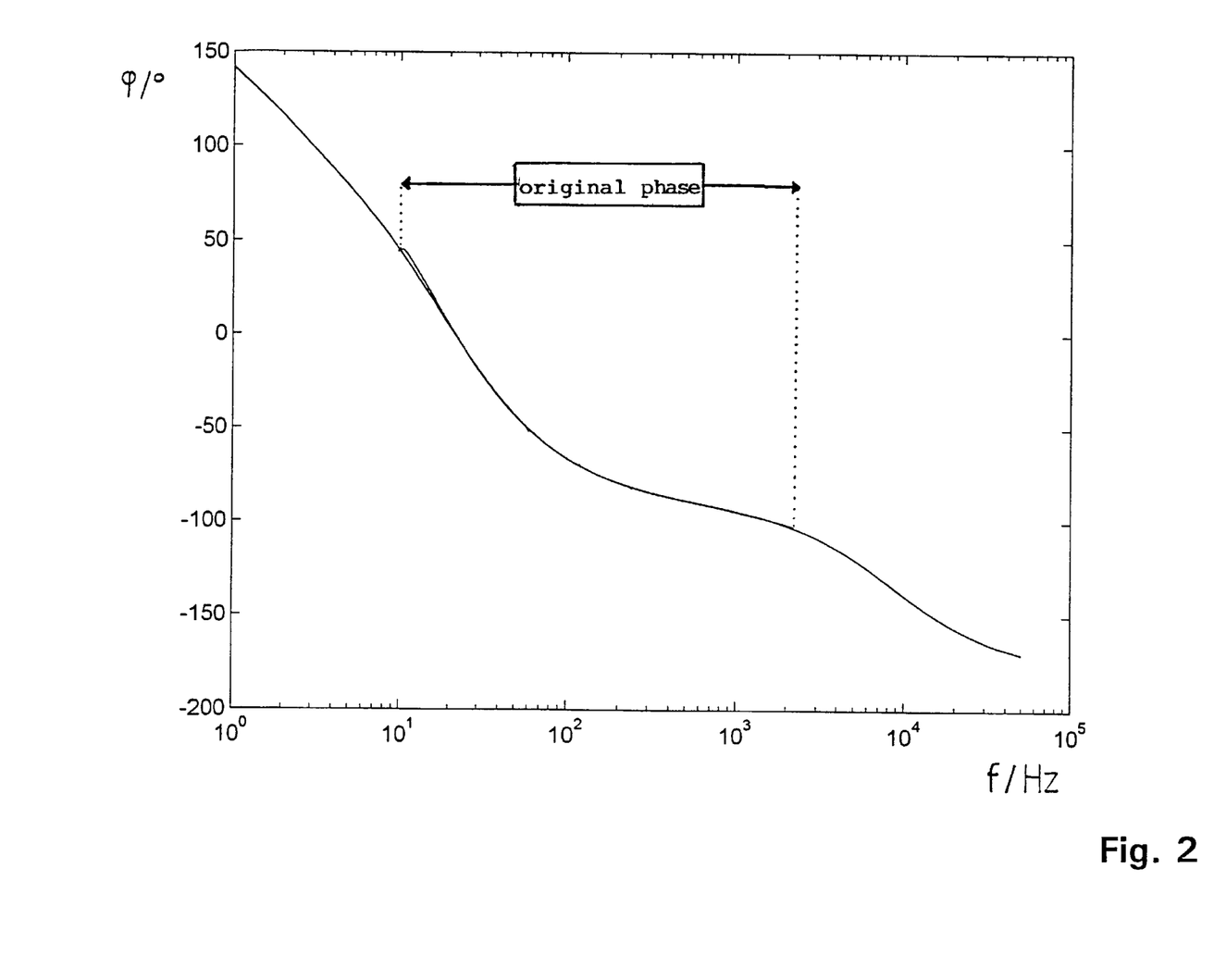
FIG. 2 shows a comparison of the original phase with the calculated phase.

In FIG. 2, the calculated phase is compared with the original phase which coincides essentially with the calculated phase and differs slightly only in the low frequency range in the direction towards larger phase angles φ.

According to the theory of linear, time-invariant and causal systems, there is a reversible relation between phase response and amplitude response such that it is sufficient to know the phase response in order to determine the amplitude response.

(c) Since the final compensation filter is to be applied to discrete sampling values, digitization of the transfer function determined according to (b) is required. The slightest distortions are obtained in general through application of the bilinear transformation. Its sampling frequency is chosen to be equal to the sampling frequency of the AD converter which serves for digitization of the (analog) effective interferograms. The discrete transfer function has the following representation in the Z-domain (if necessary with higher order):

$$H(z) = \frac{B(z)}{A(z)} = \frac{b(1) + b(2)z^{-1} + b(3)z^{-2} + b(4)z^{-3} + b(5)z^{-4} + \ldots}{a(1) + a(2)z^{-1} + a(3)z^{-2} + a(3)z^{-3} + a(5)z^{-4} + \ldots}$$

(d) The compensation filter is determined as the inverse of the discrete transfer function from (c):

$$H_{comp}(z) = \frac{A(z)}{B(z)}$$

If furthermore the denominator order of the transfer function H(s) from step (b) is larger than the numerator order, it is advantageous if the function $H_{comp}(z)$ is followed by an FIR ("finite impulse response") filter of third order with a Kaiser window for each differing order. This is to dampen the amplitude peak generated in bilinear transformation through the non-linear compression of the frequency axis.

Figure 3:
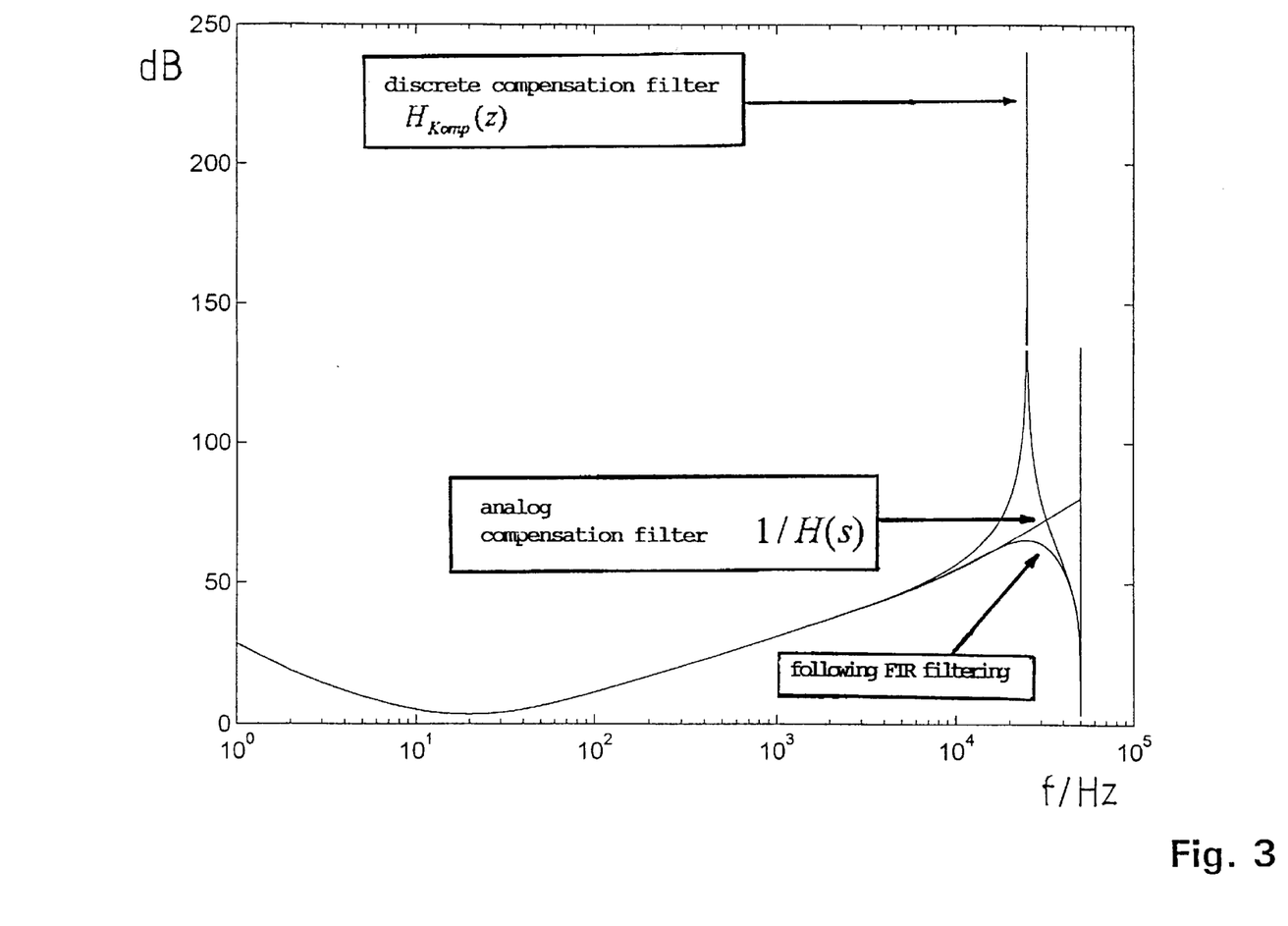
FIG. 3 shows the effect of lowpass compensation with a FIR filter on the discrete compensation filter.

In the example of FIG. 3 two FIR filters are applied. As abscissa value, the electrical frequency f measured in Hz is applied as shown in FIG. 2, whereas the ordinate value represents a value, measured in dB, of the amplitude of the filter function. One can see clearly how the discrete compensation filter $H_{comp}(z)$ terminates in a pole at high frequencies. An analog compensation filter 1/H(s) would rise in an approximately linear manner in this area. After FIR filtering which has the character of lowpass filtering, the amplitude peak of the compensation filter is eliminated.

The stability of the compensation filter $H_{comp}(z)$ is not directly guaranteed. For this reason, each instable pole is stabilized by formation of the inverse value according to the Antoniou method.

The final coefficients of the compensation filter for the DTGS detector (taken as an example) are with $$H_{comp}(z) = \frac{A(z)}{B(z)}$$

| | |
|---|---|
| b(1) | 1 |
| b(2) | 0.00000243340884 |
| b(3) | -1.99999756658855 |
| b(4) | 0.00000243340640 |
| b(5) | 0.99999756659204 |
| a(1) | 0.00283123901726 · 10³ |
| a(2) | -0.08159287090393 · 10³ |
| a(3) | 0.63737641258633 · 10³ |
| a(4) | 0.63097298553824 · 10³ |
| a(5) | -1.02686388770576 · 10³ |
| a(6) | 1.48100018639509 · 10³ |
| a(7) | 0.13107835737225 · 10³ |
| a(8) | -0.74270779162656 · 10³ |
| a(9) | 0.25477524420686 · 10³ |
| a(10) | 0.02572653766133 · 10³ |
| a(11) | 0.00080263518809 · 10³ |

In general, it mal(es sense to carry out implementation of the compensation filter and of the interpolation filter, required for converting to spatially equidistant interferogram points, on a digital signal processor (DSP). Owing to the high calculation speed with respect to filter algorithms, data processing can be carried out in real time. The filtered interferograms can be further processed with conventional software.

We claim:

1. A method of obtaining a spectrum in an optical Fourier transform (FT) spectrometer, the spectrometer having an interferometer and a detector for recording and converting optical signals from the interferometer into electrical signals as well as further signal processing elements, wherein an effective interferogram in an interesting wave length range and a reference interferogram in a narrow-band wave length range, for measuring the optical path difference, are recorded with fixed phase shift, wherein the effective interferogram is digitized in a time-equidistant manner and a digital compensation filter is applied to sampled effective signals to compensate amplitude and phase responses of the detector and the further signal processing elements, wherein the method comprises determining the compensation filter through the following steps:

a) Recording a broad-band effective interferogram during an increase and a decrease in an optical path difference in the interferometer;
   b) Carrying out a complex Fourier transformation of said effective interferogram;
   c) Forming a mean value of a phase spectrum of said recorded effective interferogram;
   d) Converting abscissa values of an averaged phase spectrum into electrical frequencies;
   e) Establishing a discrete Z-domain transfer function of the detector and the further signal processing elements, wherein free parameters of said transfer function are selected to minimize a phase response deviation of said transfer function from said mean value of step c);
   f) Determining the compensation filter as an inverse of said discrete transfer function; and
   g) Repeating steps a) through f) for each combination of detector and further signal processing elements.

2. The method of claim 1, wherein an optical path, during said increase and decrease in said optical path difference of step a), is symmetrical around a maximum of said effective interferogram.

3. The method of claim 1, wherein, in step a), a plurality of effective interferograms are recorded with different speeds of optical path increase and decrease.

4. The method of claim 3, wherein abscissa values of phase spectra of each of said recorded effective interferograms are converted to electrical frequencies and individual measuring results are subsequently averaged to a common phase response.

5. The method of claim 1, wherein step e) comprises selecting said transfer function in a linear factor representation in a Laplace domain and, on the basis of a uniform transfer function, poles and zeroes, whose values are determined successively according to a method of smallest error squares between phase response of said transfer function and said mean value of said phase spectrum of said effective interferogram recorded according to steps a) through d) are added until further improvement can no longer be achieved.

6. The method of claim 1, wherein, in step e), said transfer function is initially analog and is subsequently digitized by means of a bilinear transformation whose sampling frequency corresponds to a sampling frequency of said effective interferogram.

7. The method of claim 1, wherein, in step f), a number of lowpass filters are applied to said compensation filter, wherein said number is equal to a difference in orders of a numerator and a denominator of said transfer function.

8. The method of claim 7, wherein each of said number of lowpass filters is a finite impulse response filter.

9. The method of claim 1, further comprising eliminating instabilities of individual poles of said compensation filter by means of an Antoniou method by formation of inverse values of said poles.

10. The method of claim 1, further comprising implementing said compensation filter on a digital signal processor and transmitting data via digital interfaces to a computer for further processing.

* * * * *

UNITED STATES PATENT AND TRADEMARK OFFICE
CERTIFICATE OF CORRECTION

PATENT NO. : 5,923,422
DATED : July 13, 1999
INVENTOR(S) : Axel KEENS and Norbert RAPP It is certified that error appears in the above-identified patent and that said Letters Patent is hereby corrected as shown below:

In column 6, line 35, please replace "9υ)" with --(υ--.

In column 6, line 37, please replace $$\overline{\varphi}(\upsilon) = \frac{1}{2} \cdot (\varphi_{fwd}(\upsilon) + \varphi_{bwd}(\upsilon)) = \varphi_{el}(\upsilon)$$

with $$\overline{\Phi}(\upsilon) = \frac{1}{2} \cdot (\Phi_{fwd}(\upsilon) + \Phi_{bwd}(\upsilon)) = \Phi_{el}(\upsilon)$$

In column 6, line 43, please replace "<now" with --know.

In column 8, line 52, please replace
"b(2)    0.00000243340884" with
--b(2)   -0.00000243340884--.

UNITED STATES PATENT AND TRADEMARK OFFICE
CERTIFICATE OF CORRECTION

PATENT NO. : 5,923,422
DATED : July 13, 1999
INVENTOR(S) : Axel KEENS and Norbert RAPP It is certified that error appears in the above-identified patent and that said Letters Patent is hereby corrected as shown below:

In column 8, line 64, please replace
"a(10)     0.02572653766133·10³" with
--a(10)   -0.02572653766133·10³--

Signed and Sealed this

Twenty-ninth Day of February, 2000

Attest:

Attesting Officer

Q. TODD DICKINSON

Commissioner of Patents and Trademarks